United States Patent
Pertzov et al.

(10) Patent No.: US 8,077,307 B2
(45) Date of Patent: Dec. 13, 2011

(54) ILLUMINATION SYSTEM FOR OPTICAL INSPECTION

(75) Inventors: Ehud Pertzov, Kfar Hess (IL); Michael Matusovsky, Rishon Lezion (IL); Yaron Bar-Tal, Ganai Tikva (IL); Ilia Lutsker, Kfar Saba (IL); Ofer Ish-Shalom, Givatayim (IL)

(73) Assignee: Orbotech Ltd., Yavne (IL)

( * ) Notice: Subject to any disclaimer, the term of this patent is extended or adjusted under 35 U.S.C. 154(b) by 600 days.

(21) Appl. No.: 12/099,890

(22) Filed: Apr. 9, 2008

(65) Prior Publication Data

US 2009/0257050 A1    Oct. 15, 2009

(51) Int. Cl.
*G01N 21/00* (2006.01)

(52) U.S. Cl. ............... 356/237.1; 356/237.6; 356/239.3; 356/239.7; 382/144; 382/152

(58) Field of Classification Search .... 356/237.1–237.6, 356/239.3, 239.7; 382/144–152
See application file for complete search history.

(56) References Cited

U.S. PATENT DOCUMENTS

| | | | |
|---|---|---|---|
| 4,599,684 A | 7/1986 | Lee | |
| 5,032,735 A | 7/1991 | Kobayashi et al. | |
| 5,039,868 A | 8/1991 | Kobayashi et al. | |
| 5,245,671 A | 9/1993 | Kobayashi et al. | |
| 6,767,113 B2 | 7/2004 | Yao | |
| 6,947,151 B2 | 9/2005 | Fujii et al. | |
| 7,062,080 B2 | 6/2006 | Oshiumi et al. | |
| 7,557,920 B2 * | 7/2009 | Lebens | 356/394 |
| 7,751,611 B2 * | 7/2010 | Akiyama et al. | 382/147 |
| 2005/0190361 A1 | 9/2005 | Ishiba et al. | |
| 2006/0000989 A1 | 1/2006 | Kuriyama et al. | |
| 2006/0291713 A1 | 12/2006 | Moriya et al. | |

FOREIGN PATENT DOCUMENTS

| | | |
|---|---|---|
| EP | 0231941 | 8/1987 |
| EP | 0685732 | 12/1995 |
| EP | 1314974 | 5/2003 |
| EP | 1568985 | 8/2005 |
| EP | 1612569 | 1/2006 |
| JP | 1282410 | 11/1989 |
| JP | 4166710 | 6/1992 |
| JP | 4166711 | 6/1992 |
| JP | 7012748 | 1/1995 |
| JP | 8166218 | 6/1996 |
| JP | 2003227801 | 8/2003 |
| JP | 2006047290 | 2/2006 |
| JP | 2006322951 | 11/2006 |

* cited by examiner

*Primary Examiner* — Gregory J Toatley
*Assistant Examiner* — Iyabo S Alli
(74) *Attorney, Agent, or Firm* — Sughrue Mion, PLLC (57) ABSTRACT

Apparatus for optical inspection includes an illumination assembly, including multiple parallel rows of light sources for emitting light and illumination optics associated with each row for directing the light onto an object under inspection. The multiple parallel rows include at least a first row with first illumination optics including a first array of prisms that are configured to reflect the light emitted by the light sources in the first row, and at least a second row with second illumination optics including a second array of prisms that are configured to refract the light emitted by the light sources in the second row. An imaging assembly is configured to capture an image of the object under illumination by the multiple parallel rows of the light sources.

36 Claims, 7 Drawing Sheets

ILLUMINATION SYSTEM FOR OPTICAL INSPECTION

FIELD OF THE INVENTION

The present invention relates generally to optical inspection, and specifically to illumination systems for use in optical inspection.

BACKGROUND OF THE INVENTION

The ability of a system for automated optical inspection (AOI) to detect defects quickly and reliably can be strongly affected by the quality of illumination of the object under inspection. Both the intensity and the symmetry of the illumination can be important in this regard. For this reason, AOI illumination systems commonly use multiple light sources with various types of illumination optics.

For example, U.S. Pat. Nos. 5,032,735, 5,039,868, and 5,245,671, whose disclosures are incorporated herein by reference, describe apparatus for inspecting printed circuit boards that uses a plurality of ring-shaped light sources to illuminate the board. The light sources may emit light of different colors.

As another example, U.S. Patent Application Publication 2005/0190361, whose disclosure is incorporated herein by reference, describes apparatus for inspecting a substrate in which the substrate is irradiated by red, green and blue light beams at different elevation angles.

U.S. Patent Application Publication 2006/0000989, whose disclosure is incorporated herein by reference, describes an illumination device for inspecting a substrate in which a plurality of multi-colored light emitting members are set around the optical axis of a camera above the substrate.

SUMMARY OF THE INVENTION

In the embodiments of the present invention that are described hereinbelow, an inspection system comprises an illumination assembly that uses multiple parallel rows of light sources to provide nearly symmetrical illumination of the object under inspection. Specifically, these embodiments use arrays of prisms in novel configurations to deflect (by refraction or reflection) the light emitted by the light sources so that the light strikes the object from multiple different angles.

There is therefore provided, in accordance with an embodiment of the present invention, apparatus for optical inspection, including:

an illumination assembly, including multiple parallel rows of light sources for emitting light and illumination optics associated with each row for directing the light onto an object under inspection, the multiple parallel rows including:

at least a first row with first illumination optics including a first array of prisms that are configured to reflect the light emitted by the light sources in the first row; and at least a second row with second illumination optics including a second array of prisms that are configured to refract the light emitted by the light sources in the second row; and an imaging assembly, which is configured to capture an image of the object under illumination by the multiple parallel rows of the light sources.

In a disclosed embodiment, the multiple parallel rows include at least a third row of the light sources with third illumination optics of a third type for illuminating the object directly, without incidence of light from the light sources in the third row on a prism array. In some embodiments, the light sources in at least some of the multiple parallel rows emit light of different, respective colors. In one embodiment, the light sources include light-emitting diodes (LEDs) having a rated maximum current, and the illumination assembly includes a driver circuit, which is configured to drive the LEDs with current pulses in excess of the rated maximum current.

In some embodiments, the illumination assembly has a plane of symmetry that intersects the object along a line, and the imaging assembly is configured to capture the image of a region of the object that contains at least a part of the line. Typically, the apparatus includes a motion assembly, which is configured to cause the illumination and imaging assemblies to scan over the object in a direction perpendicular to the line. Additionally or alternatively, the multiple parallel rows of the light sources are arranged in pairs of the rows, which define respective pairs of illumination planes that intersect the line at respective equal and opposite elevation angles on opposing sides of the plane of symmetry. Further additionally or alternatively, the image assembly includes a plurality of cameras, which are configured to capture respective images that are mutually adjacent and each contain a respective part of the line.

There is also provided, in accordance with an embodiment of the present invention, apparatus for optical inspection of an object, including:

an illumination assembly, which has a plane of symmetry that intersects the object along a line, and which includes:

first and second parallel rows of light sources, which are configured to emit light along respective optical axes, wherein the optical axes are oriented toward the object in respective first and second illumination planes that intersect the line at respective first and second equal and opposite elevation angles on opposing sides of the plane of symmetry; and first and second arrays of prisms, which are disposed respectively in the first and second illumination planes, and which are configured to divert the light emitted by the light sources so that the light impinges on the object along directions diagonal to the line; and an imaging assembly, which is configured to capture an image of a region of the object that contains the line under illumination by the illumination assembly.

In a disclosed embodiment, the prisms in the first and second arrays have prism axes that are respectively perpendicular to the first and second illumination planes, and are configured to refract the light so that the directions in which the light is diverted by the prisms fall within one of the first and second illumination planes. The light source and prisms may be arranged so that at least a portion of the light impinging on the object intersects the line at intersection angles that are within 10° of the plane of symmetry.

There is additionally provided, in accordance with an embodiment of the present invention, apparatus for optical inspection of an object, including:

an illumination assembly, which has a plane of symmetry that intersects the object along a line, and which includes multiple parallel rows of light sources for emitting light and illumination optics associated with each row for directing the light onto the object, the multiple parallel rows including:

first and second rows of the light sources with respective first and second illumination optics that are configured to direct the light from the light sources in the first and second rows to impinge on the object in respective first and second illumination planes that intersect the line at respective first and second equal and opposite elevation angles on opposing sides of the plane of symmetry; and third and fourth rows of the light sources with respective third and fourth illumination optics including arrays of prisms that are configured to divert the light from the light sources in the third and fourth rows toward the object in respective third and fourth illumination planes that intersect the line at respective third and fourth equal and opposite elevation angles on the opposing sides of the plane of symmetry; and an imaging assembly, which is configured to capture an image of the object under illumination by the multiple parallel rows of the light sources.

Typically, the arrays of prisms are configured to divert the light emitted by the light sources so that the light impinges on the object along directions diagonal to the line. In a disclosed embodiment, the arrays of the prisms have respective prism axes that are respectively perpendicular to the third and fourth illumination planes, and are configured to divert the light so that the directions in which the light is diverted by the prisms fall within one of the third and fourth illumination planes.

In one embodiment, the arrays of the prisms are configured to reflect the light from the light sources in the third and fourth rows toward the object.

There is further provided, in accordance with an embodiment of the present invention, apparatus for optical inspection of an object, including:

an illumination assembly, which has a plane of symmetry that intersects the object along a line, and which includes:
multiple parallel rows of light sources, which are configured to emit light in respective illumination planes that intersect the line on opposing sides of the plane of symmetry; and
illumination optics, which are configured to divert the light emitted by the light sources so that at least a part of the light impinges on the object along directions in the illumination planes that intersect the line at intersection angles that are within 10° of the plane of symmetry; and
an imaging assembly, which is configured to capture an image of a region of the object that contains the line under illumination by the illumination assembly.

The illumination optics may be configured to divert the light emitted by the light sources so that at least some of the light impinges on the object along directions in the illumination planes that intersect the line at intersection angles that are within 5° of the plane of symmetry.

Typically, the rows of the light sources have respective ends, and the illumination assembly includes at least one end mirror, adjacent and perpendicular to the ends of the rows, for reflecting at least a portion of the light diverted by the optics onto the object.

There is moreover provided, in accordance with an embodiment of the present invention, a method for optical inspection, including:

illuminating an object under inspection using multiple parallel rows of light sources for emitting light and illumination optics associated with each row for directing the light onto the object, the multiple parallel rows including:
at least a first row with first illumination optics including a first array of prisms that are configured to reflect the light emitted by the light sources in the first row; and
at least a second row with second illumination optics including a second array of prisms that are configured to refract the light emitted by the light sources in the second row; and
capturing an image of the object under illumination by the multiple parallel rows of the light sources.

There is furthermore provided, in accordance with an embodiment of the present invention, a method for optical inspection of an object, including:

illuminating the object using an illumination assembly, which has a plane of symmetry that intersects the object along a line, and which includes:
first and second parallel rows of light sources, which are configured to emit light along respective optical axes, wherein the optical axes are oriented toward the object in respective first and second illumination planes that intersect the line at respective first and second equal and opposite elevation angles on opposing sides of the plane of symmetry; and
first and second arrays of prisms, which are disposed respectively in the first and second illumination planes, and which are configured to divert the light emitted by the light sources so that the light impinges on the object along directions diagonal to the line; and
capturing an image of a region of the object that contains the line under illumination by the illumination assembly.

There is also provided, in accordance with an embodiment of the present invention, a method for optical inspection of an object, including:

illuminating the object using an illumination assembly, which has a plane of symmetry that intersects the object along a line, and which includes multiple parallel rows of light sources for emitting light and illumination optics associated with each row for directing the light onto the object, the multiple parallel rows including:
first and second rows of the light sources with respective first and second illumination optics that are configured to direct the light from the light sources in the first and second rows to impinge on the object in respective first and second illumination planes that intersect the line at respective first and second equal and opposite elevation angles on opposing sides of the plane of symmetry; and
third and fourth rows of the light sources with respective third and fourth illumination optics including arrays of prisms that are configured to divert the light from the light sources in the third and fourth rows toward the object in respective third and fourth illumination planes that intersect the line at respective third and fourth equal and opposite elevation angles on the opposing sides of the plane of symmetry; and
capturing an image of the object under illumination by the multiple parallel rows of the light sources.

There is additionally provided, in accordance with an embodiment of the present invention, a method for optical inspection of an object, including:

illuminating the object using an illumination assembly, which has a plane of symmetry that intersects the object along a line, and which includes:
multiple parallel rows of light sources, which are configured to emit light in respective illumination planes that intersect the line on opposing sides of the plane of symmetry; and
illumination optics, which are configured to divert the light emitted by the light sources so that at least a part of the light impinges on the object along directions in the illumination planes that intersect the line at intersection angles that are within 10° of the plane of symmetry; and
an imaging assembly, which is configured to capture an image of a region of the object that contains the line under illumination by the illumination assembly.

The present invention will be more fully understood from the following detailed description of the embodiments thereof, taken together with the drawings in which:

DETAILED DESCRIPTION OF EMBODIMENTS

Figure 1:
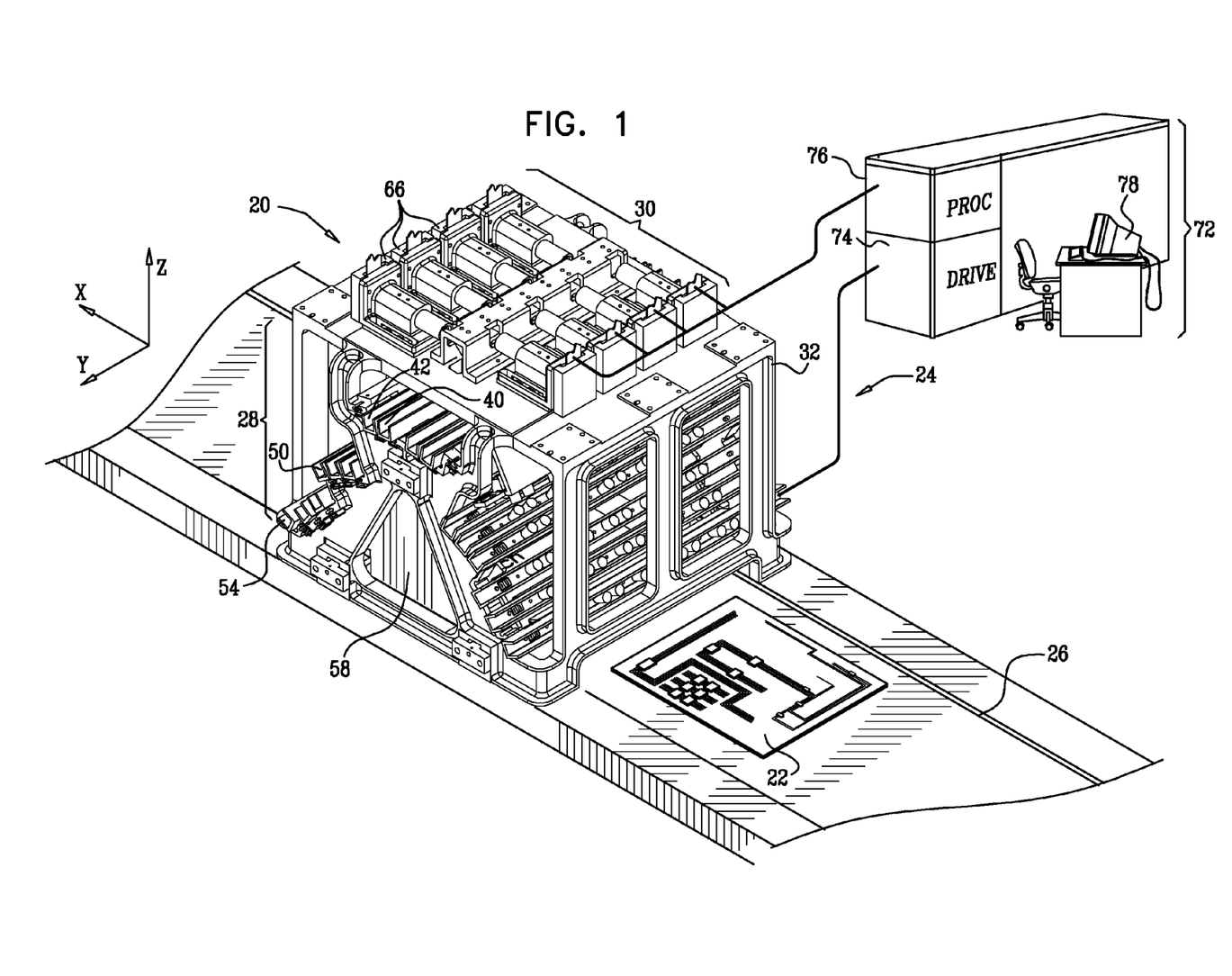
FIG. 1 is a schematic, pictorial illustration of a system for AOI, in accordance with an embodiment of the present invention.

FIG. 1 schematic, pictorial illustration of a system 20 for AOI of an object, in accordance with an embodiment of the present invention. System 20 in this embodiment is assumed, for the sake of illustration, to be used for inspection of an assembled printed circuit board (PCB) 22, although the principles of the present invention may similarly be applied in inspection of other sorts of objects. PCB 22 is transported by a motion assembly 26, such as a moving belt or translation stage, through an optical assembly 24, which performs the actual inspection. Alternatively or additional, the motion assembly may move the optical assembly relative to the PCB. For the sake of convenience in the description that follows, PCB 22 is assumed to lie in the XY plane, and motion assembly 26 is assumed to cause optical assembly 24 to scan over the PCB in the X-direction, as indicated by the axes marked in the figure.

Figure 2:
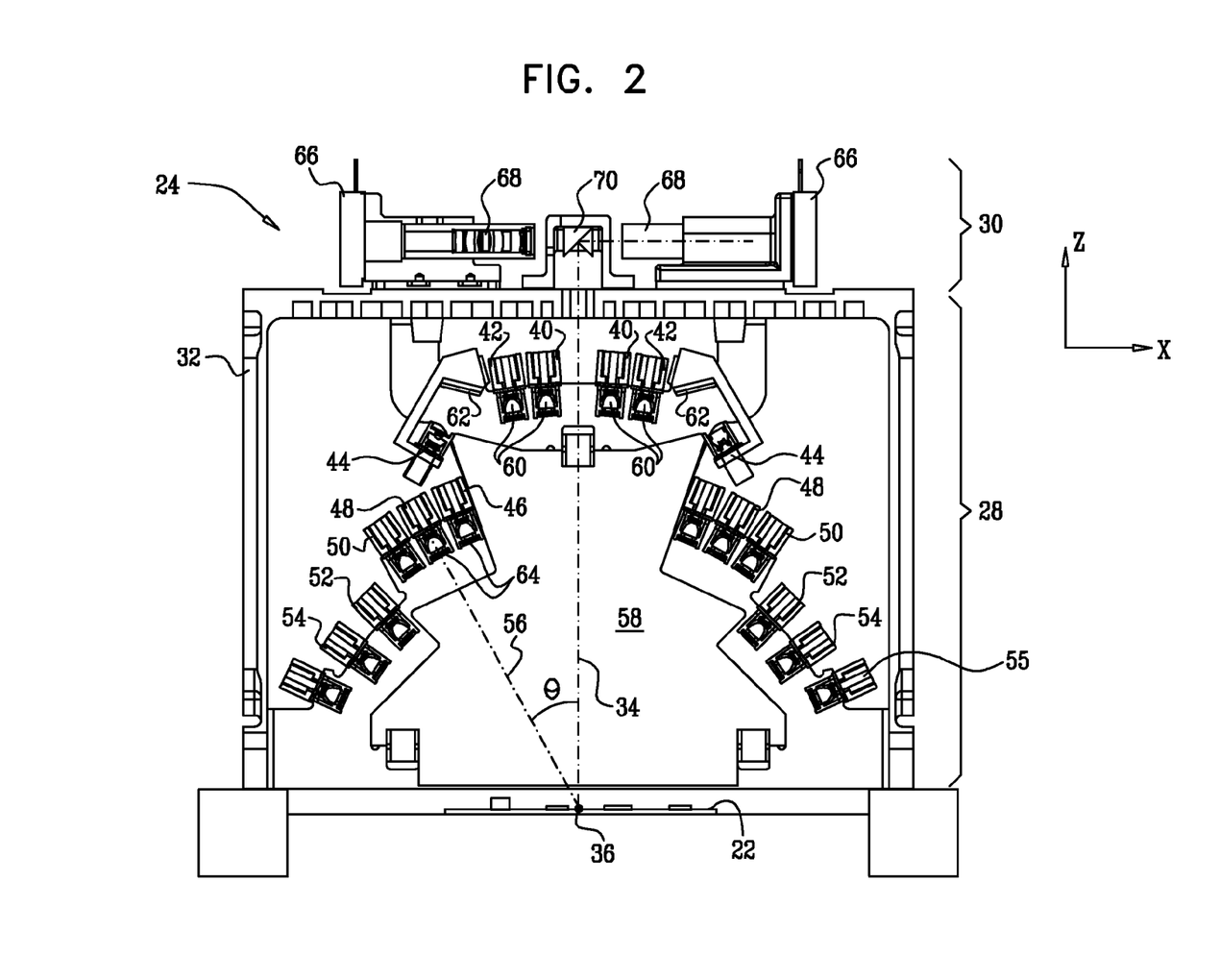
FIG. 2 is a schematic, sectional view of an illumination assembly, in accordance with an embodiment of the present invention.

FIG. 2 is a schematic, sectional view of optical assembly 24, taken in the XZ plane, in accordance with an embodiment of the present invention. The description that follows refers to this figure together with FIG. 1. Optical assembly 24 comprises an illumination assembly 28 and an imaging assembly 30, which are mounted on a frame 32. (Although frame 32 is shown in the figures as a unitary unit of a certain shape, other frame configurations may alternatively be used, including separate frames for the illumination and imaging assemblies, for example.) As can be seen in the figures, illumination assembly 28 is symmetrical about a YZ plane 34. This plane intersects PCB 22 along a line 36, which is oriented in the Y-direction. Imaging assembly 30 captures images of a region of the PCB that contains line 36.

Figure 3:
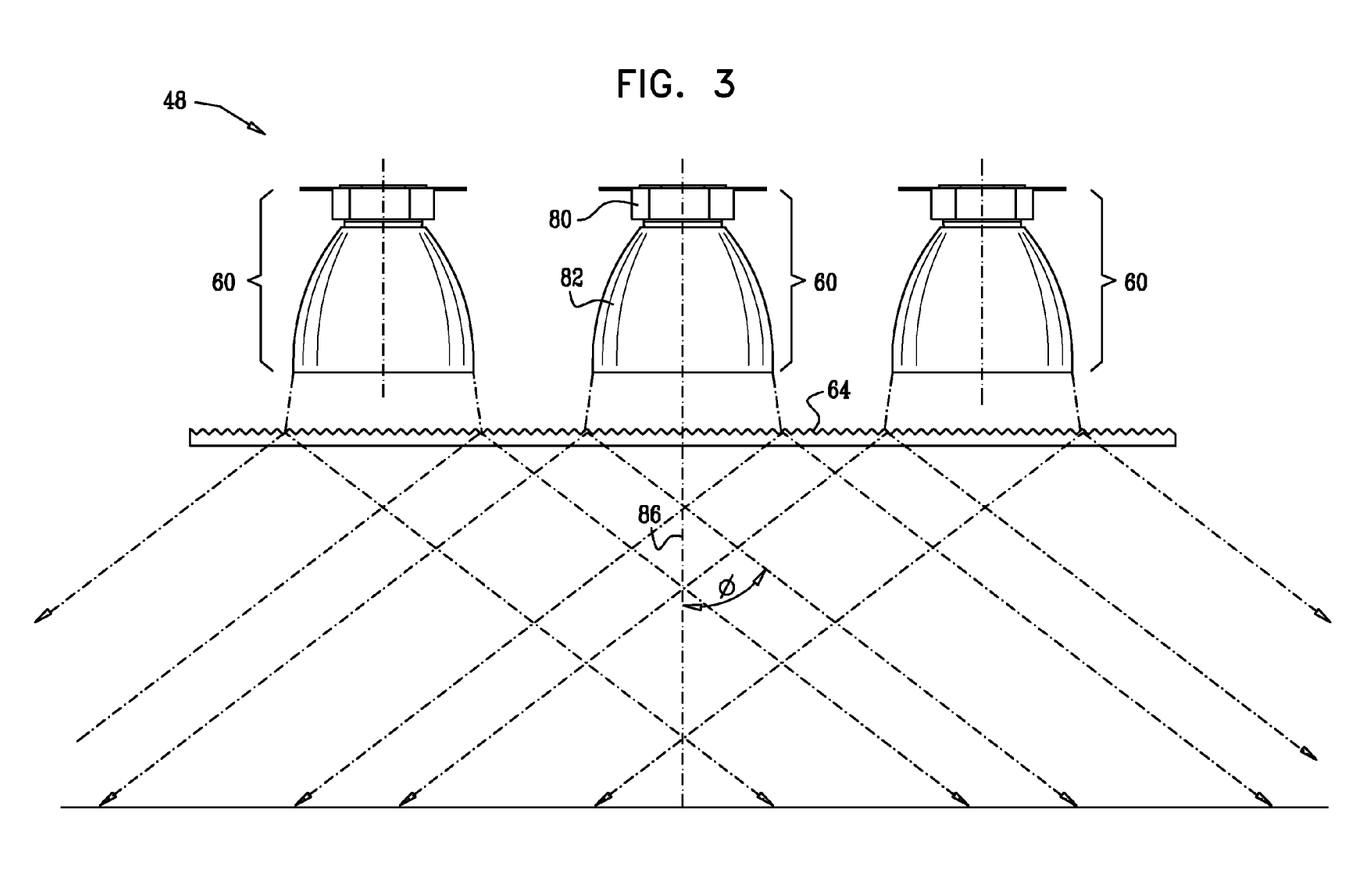
FIG. 3 is a schematic side view of a row of illumination sources and associated optics, in accordance with an embodiment of the present invention.
Figure 5:
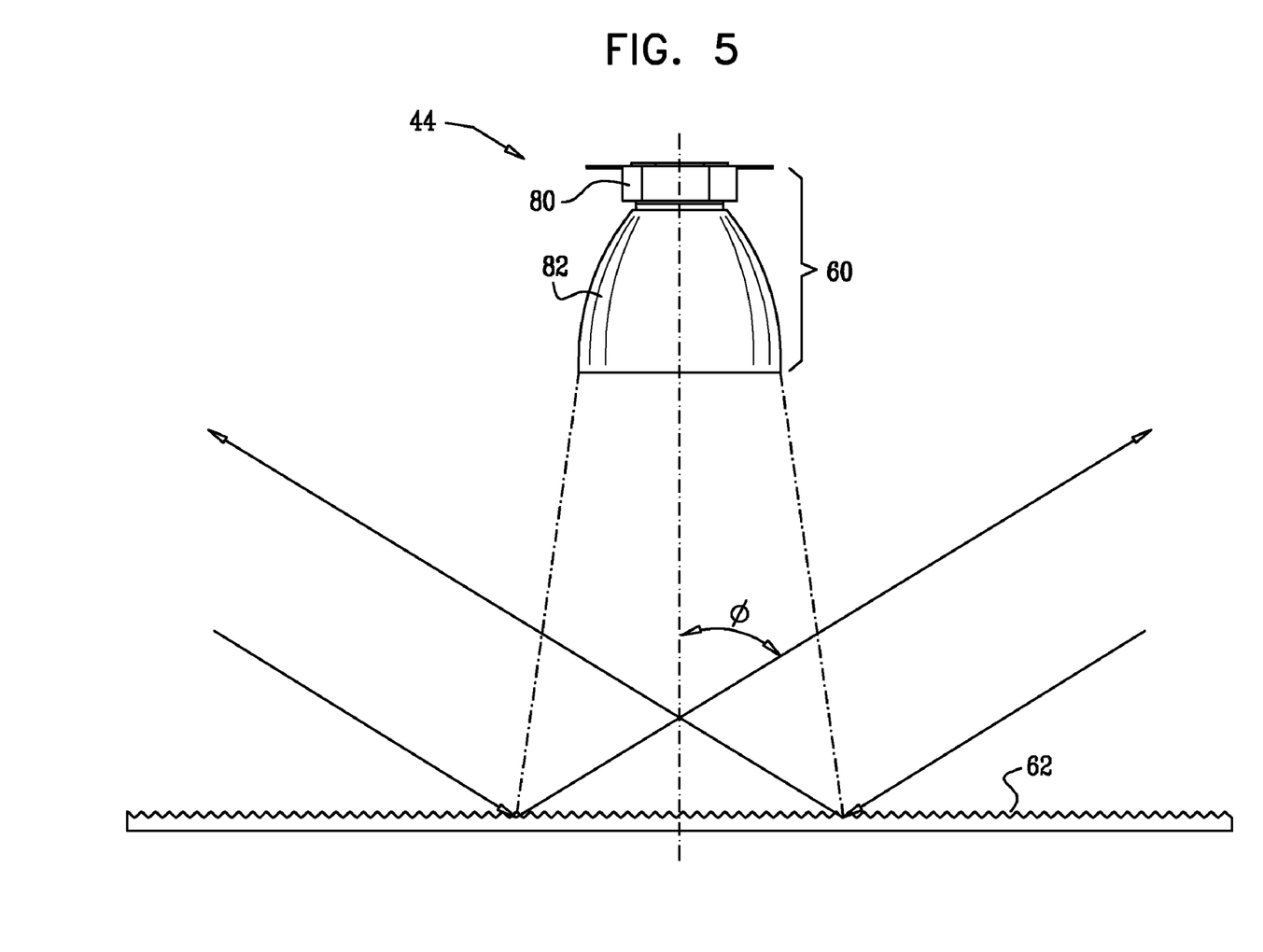
FIG. 5 is a schematic side view of an illumination source and associated optics, in accordance with another embodiment of the present invention.

Illumination assembly 28 comprises multiple parallel rows 40, 42, 44, 46, 48, 50, 52, 54, 55 of light sources 60, which extend across the illumination assembly in the Y-direction. The rows typically have associated illumination optics, which may comprise a reflective prism array 62 or a refractive prism array 64, as explained further hereinbelow. Additionally or alternatively, the illumination optics may comprise a collimator, as illustrated in FIGS. 3 and 5, as well as other components, such as a diffuser (not shown). The light sources in each of the rows have parallel optical axes, such as an axis 56 that is shown in FIG. 2, which together define the illumination plane of that row. The elevation angle of each row is defined by the angle θ between this illumination plane and the plane of symmetry (plane 34). (For rows having reflective optics, such as reflective prism array 62, the illumination plane is defined by the directions of the optical axes of the light sources following reflection from the optics.) For symmetrical illumination along the X-direction, rows 40, 42, 44, 46, 48, 50, 52, 54, 55 are arranged in pairs, with respective illumination planes at equal and opposite elevation angles on the opposing sides of the plane of symmetry.

For symmetry of illumination along the Y-direction, the illumination optics, such as prism arrays 62 and 64, typically spread the light in the Y-direction. Furthermore, illumination assembly 28 may comprise end mirrors 58 at the ends of the rows of light sources at both sides of the assembly, in order reflect light that strikes the end mirrors back onto PCB 22. The end mirrors, in effect, create duplicate virtual light sources extending in the Y-direction beyond the actual bounds of the illumination assembly.

Imaging assembly 30 comprises multiple cameras 66 with respective imaging optics 68. In the embodiment shown in the figures, the cameras are arranged on alternating sides of plane 34, with reflectors 70 for aiming the respective optical axes of the cameras along the plane. This arrangement permits the fields of view of the cameras to be packed closely together. Alternatively, the cameras may view the object under inspection directly, without reflectors. In the pictured embodiment, there are eight cameras, each with a respective two-dimensional image sensor.

Cameras 66 and optics 68 are arranged so that the fields of view of the cameras adjoin one another, typically with some overlap between neighboring fields of view. The cameras thus provide a set of electronic images that may cover the area of line 36 across the entire width (Y-dimension) of PCB 22. Alternatively, the imaging assembly may comprise a larger or smaller number of cameras (possibly even a single camera). Further alternatively, the imaging assembly may comprise a one-dimensional, linear sensor array or time-domain integration (TDI) sensor array, as are known in the art. In any case, as motion assembly advances PCB 22, the cameras typically capture successive images, each displaced in the X-direction with respect to its predecessor, so that the imaging assembly images the entire area of the PCB (or at least the entire area that is of interest for inspection purposes). System 20 may be operated so that the cameras capture images while the PCB is in motion relative to the optical assembly or, alternatively, the motion may be stopped during image capture. In one embodiment, the imaging assembly captures successive images of the same area of the PCB under different illumination conditions, such as different colors of illumination.

Operation of system 20 is controlled by a console 72 (FIG. 1). The console comprises illumination driver circuits 74, which provide power to light sources 60. An image processor 76 receives and processes the electronic images captured by cameras 66. Typically, processor 76 analyzes the images, according to predefined criteria, in order to detect defects in PCB 22 and/or in the components that are assembled on the PCB. This processor may comprise a general-purpose computer with suitable software and interface circuits. Alternatively or additionally, the processor may comprise dedicated or programmable hardware logic circuits. The processor provides an output via an interface device 78, such as a computer monitor, indicating the types and locations of the defects found in each PCB, or indicating that no defects were found.

FIG. 3 is a schematic side view showing light sources 60 in row 48, in accordance with an embodiment of the present invention. This particular row is chosen by way of example, and certain characteristics of the row are common to other rows of light sources in illumination assembly 28, as well. For the sake of simplicity, only three light sources are shown in FIG. 3, but in practice each row may comprise a larger number of light sources, such as between fifteen and twenty light sources, depending on the light source characteristics, the optical geometry and the width of the object that is under inspection.

Each light source 60 in this example comprises a light emitter 80 and a collimating optic 82, which serves as a part of the illumination optics. Each light source has an optical axis 86, which is defined by the geometry of the emitter and optics. Any suitable type of light emitter may be used in this context, with any suitable emission wavelength or wavelength range. In this context, the term "light" should be understood to comprise any type of optical radiation, including ultraviolet and infrared, as well as visible light. Furthermore, different rows of light sources, or even different light sources within a single row, may be configured to emit light of different colors. For example, in one embodiment, rows 40 and 42 emit red light, rows 44, 52 and 54 emit blue light, row 48 emits green light, and rows 46, 50 and 55 emit white light. This selection of colors is useful in detecting different types of defects in PCB 22.

In some embodiments, each light emitter 80 comprises a high-power light-emitting diode (LED), which is driven by driver circuits 74 at an average level of at least 700 mW per LED, and possibly more than 1 W per LED. For example, the LEDs in assembly 28 may be Luxeon® K2 LEDs, produced by Philips Lumileds Lighting Company (San Jose, Calif.). In order to capture images in system 20 without blur during scanning by motion assembly 26, circuits 74 drive the LEDs in pulsed mode, typically with pulse duration of about 240 µs and pulse repetition frequency of 6 Hz. Although the maximum driving current recommended for the LEDs by the manufacturer is 1 A, the inventors have found that it is possible to drive the LEDs in pulsed mode at much higher current, typically at least 4 A peak current, and possibly as high as 10 A, and thus to obtain much greater light output. The high power is useful in providing sufficient illumination intensity in a short pulse to permit cameras 66 to capture clear images without blurring. The specific values of current, duration and repetition frequency given above are presented by way of example, and other pulse parameters may alternatively be used, depending on application requirements and the properties of the light sources.

Prism array 64 refracts the light emitted by light sources 60. The prism array may comprise, for example, a microprism array produced by Reflexite Americas (New Britain, Conn.). As can be seen in FIG. 3, this array comprises multiple parallel prisms, having prism axes that are perpendicular to the illumination plane that is defined by the optical axes of the light sources. (In the view shown in FIG. 3, the illumination plane is the plane of the figure itself, while the prism axes extend in the direction perpendicular to the page, along the ridges of the prisms.) In one embodiment, the prisms are spaced 3 mm apart, and the prism angles are chosen so that collimated light emitted by the light sources is diverted within the illumination plane by a desired angle φ, such as φ=25°. As a result, the light diverted by prism array 64 travels diagonally within the illumination plane and thus impinges on PCB 22 along directions that are diagonal (non-perpendicular) to line 36.

On the other hand, because the prism axes are perpendicular to the illumination plane of row 48, the prism array does not substantially divert the light out of the illumination plane. Therefore, the light emitted by light sources 60 remains roughly within the illumination plane and thus impinges on PCB 22 in the area of line 36 at elevation angles that are within about 5° of the elevation angle of the illumination plane relative to plane 34 (FIG. 2).

Typically, most, but not all, of the rows of light sources in illumination assembly 28 comprise refractive prism arrays, like row 48, and are arranged in a fashion similar to that described above. The prism angles may be the same as or different from those in the prism array used for row 48. On the other hand, in the present embodiment, for example, row 44 uses reflective prism array 62, as will be explained in greater detail hereinbelow. Other rows, such as rows 40 and 54, may be configured to illuminate the area of line 36 directly, i.e., without incidence of the light from the light sources in these rows on any prism array. The inventors have found that these particular row configurations give good results in terms of symmetry of illumination, but other arrangements of illumination colors and optics may alternatively be used.

Figure 4:
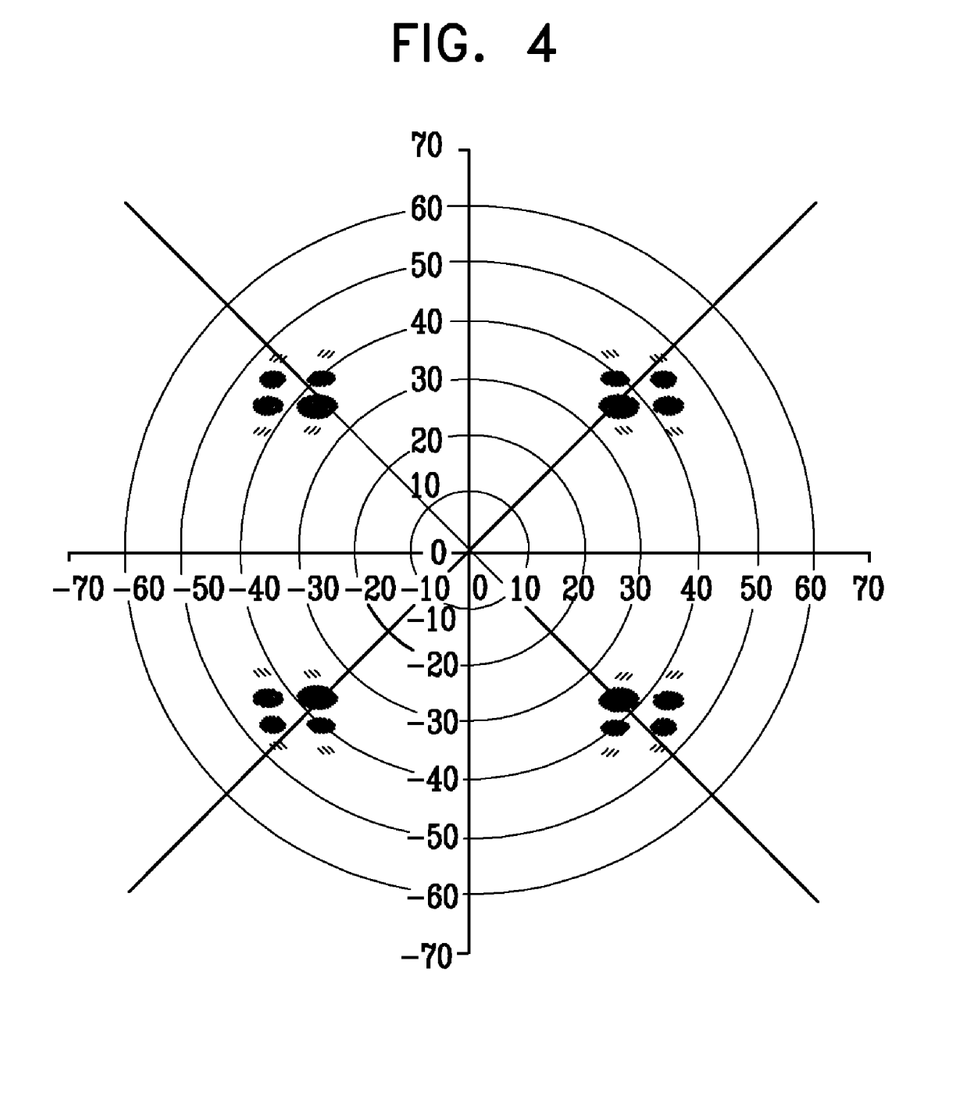
FIG. 4 is a schematic plot of light intensity distribution generated by an illumination assembly, in accordance with an embodiment of the present invention.

FIG. 4 is a schematic plot of light intensity distribution generated by light sources 60 and prism array 64 in row 48, in accordance with an embodiment of the present invention. This plot shows the intensity as a function of incidence angle on PCB 22, as would be seen by an observer located at any point along line 36. (The use of a dense row of light sources along with end mirrors 58 ensures that the lighting is uniform over the entire length of the line.) To generate this plot, row 48 was located at an elevation angle θ=28.5°, and prism array 64 was designed to give the deviation angle φ=25°, as noted above. As a result of this configuration, the intensity pattern of the light incident on line 36 is very nearly symmetrical with respect to the XY and XZ planes. This sort of symmetry is useful in ensuring that system 20 detects all defects in PCB 22 reliably and without artifacts due to inhomogeneous illumination.

Figure 6:
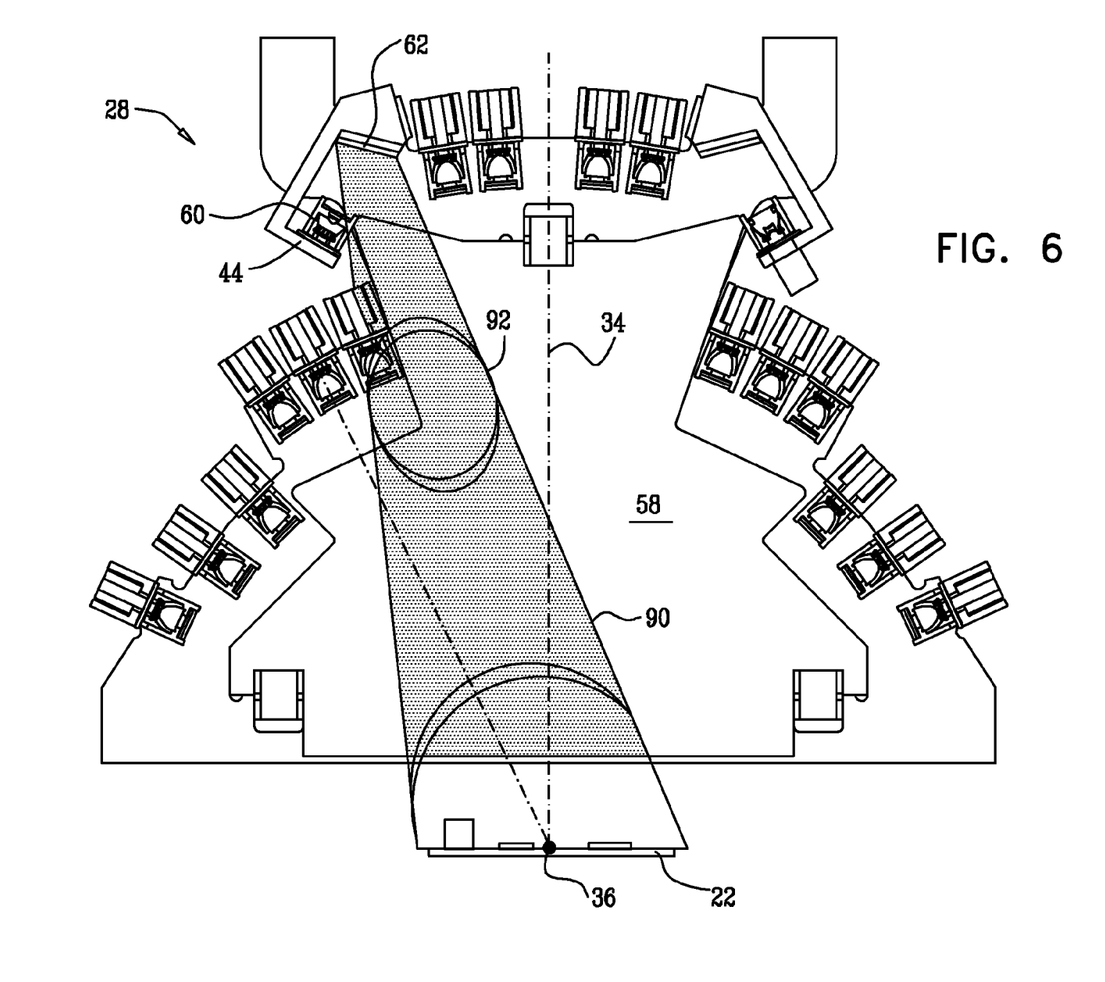
FIG. 6 is a schematic, sectional view of an illumination assembly, illustrating a beam of light generated by a light source in the assembly, in accordance with an embodiment of the present invention.
Figure 7:
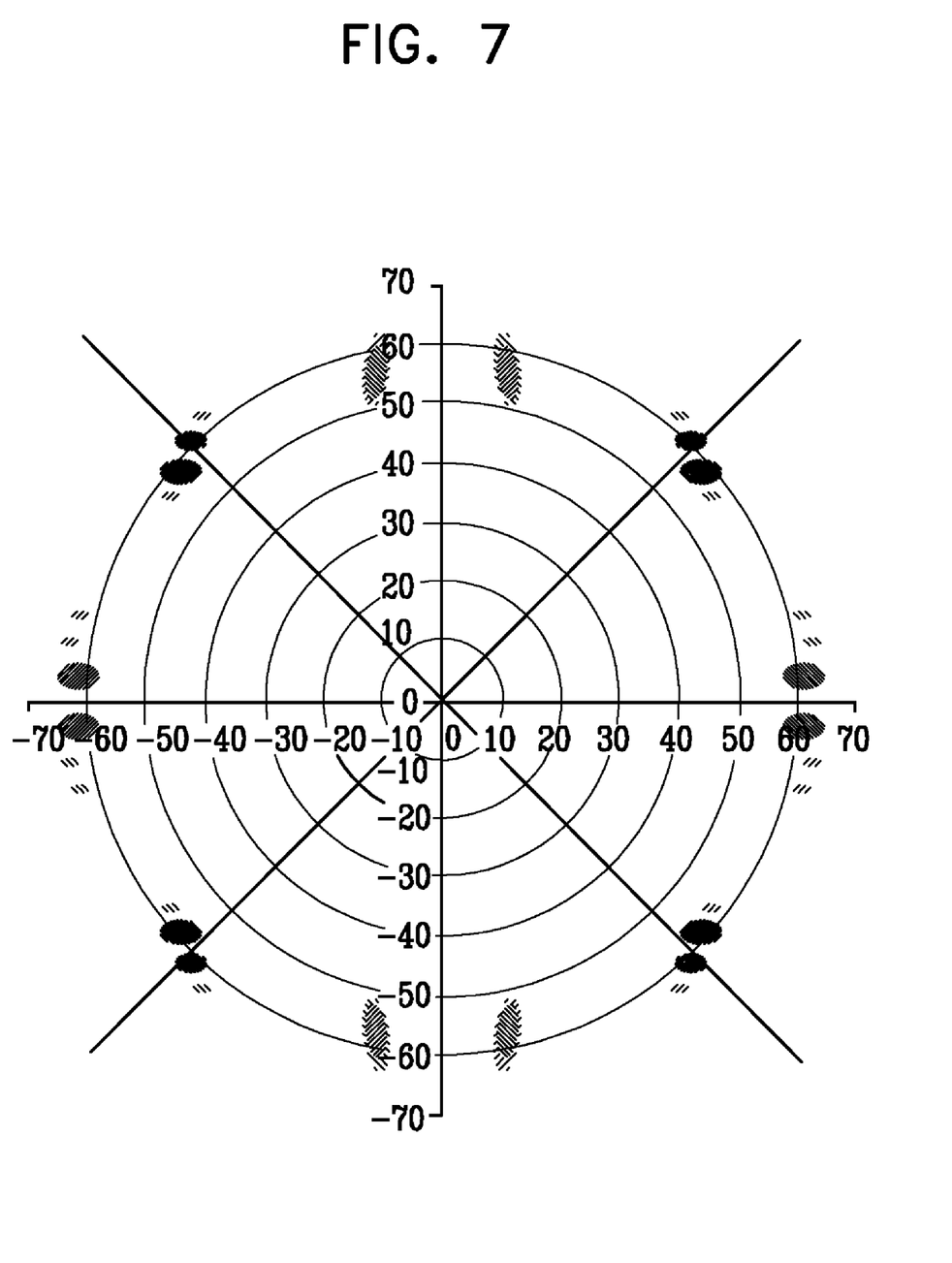
FIG. 7 is a schematic plot of light intensity distribution generated by an illumination assembly, in accordance with another embodiment of the present invention.

Reference is now made to FIGS. 5-7, which schematically illustrate the use of reflective prism array 62 with light sources 60 in row 44, in accordance with an embodiment of the present invention. FIG. 5 is a side view of one of the light sources in the row, while FIG. 6 is a sectional view of illumination assembly 28 showing propagation of a beam 90 emitted by one of these light sources. FIG. 7 shows the light intensity distribution generated by light sources 60 and prism array 62 in row 48, together with the light sources in row 54.

Array 62 typically comprises prisms of similar spacing and prism angles to those used in the refractive prism arrays described above, except that the surface of array 62 facing light sources 60 has a reflective coating. Because of the different geometrical characteristics of reflection and refraction, array 62 typically diverts the light emitted by sources 60 at a greater angle φ within the illumination plane than the diversion due to the refractive prism arrays.

In the example shown in FIG. 6, prism array 62 is configured so that the illumination plane of row 44 has an elevation angle of about 15° relative to plane 34 (which is perpendicular to the plane of FIG. 6), and the prism angles of the array are chosen to give a deviation angle of φ=55°. Consequently, light from sources 60 in row 44 is incident on PCB 22 in the area of line 36 along directions that are nearly parallel to plane 34. Beam 90, in fact, reflects from an area 92 of end mirror 58 and then strikes the PCB along this direction. In the pictured configuration, at least a part of the light from row 44 impinges on the PCB along directions in the illumination plane that are within 10° of the plane of symmetry. Alternatively, if row 44 is moved to a smaller elevation angle relative to plane 34, at least a part of the light can be made to impinge along directions within 5° of the plane of symmetry.

At the same time, other rows, such as rows 54, may be configured to illuminate the area of line 32 directly, with the same color of illumination as rows 44. As can be seen in FIG. 2, direct illumination from light sources 60 in row 54, without an intervening prism array, strikes the area of line 36 on PCB 22 along a direction that is nearly parallel to the X-axis. The combination of this illumination with the reflected illumination due to rows 44 again gives a nearly-symmetrical pattern of light intensity on PCB 22. The result is shown in FIG. 7.

Although the operation of illumination assembly 28 is described hereinabove in the context of a particular type of system for AOI, the principles of the present invention may similarly be applied to illumination in other types of inspection systems, as well as illumination in other applications that require intense, homogeneous lighting. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for optical inspection, comprising:
    an illumination assembly, comprising multiple parallel rows of light sources for emitting light and illumination optics associated with each row for directing the light onto an object under inspection, the multiple parallel rows comprising:
    at least a first row with first illumination optics comprising a first array of prisms that are configured to reflect the light emitted by the light sources in the first row; and
    at least a second row with second illumination optics comprising a second array of prisms that are configured to refract the light emitted by the light sources in the second row; and
    an imaging assembly, which is configured to capture an image of the object under illumination by the multiple parallel rows of the light sources.

2. The apparatus according to claim 1, wherein the multiple parallel rows comprise at least a third row of the light sources with third illumination optics of a third type for illuminating the object directly, without incidence of light from the light sources in the third row on a prism array.

3. The apparatus according to claim 1, wherein the light sources in at least some of the multiple parallel rows emit light of different, respective colors.

4. The apparatus according to claim 1, wherein the light sources comprise light-emitting diodes (LEDs) having a rated maximum current, and wherein the illumination assembly comprises a driver circuit, which is configured to drive the LEDs with current pulses in excess of the rated maximum current.

5. The apparatus according to claim 1, wherein the illumination assembly has a plane of symmetry that intersects the object along a line, and wherein the imaging assembly is configured to capture the image of a region of the object that contains at least a part of the line.

6. The apparatus according to claim 5, and comprising a motion assembly, which is configured to cause the illumination and imaging assemblies to scan over the object in a direction perpendicular to the line.

7. The apparatus according to claim 5, wherein the multiple parallel rows of the light sources are arranged in pairs of the rows, which define respective pairs of illumination planes that intersect the line at respective equal and opposite elevation angles on opposing sides of the plane of symmetry.

8. The apparatus according to claim 5, wherein the image assembly comprises a plurality of cameras, which are configured to capture respective images that are mutually adjacent and each contain a respective part of the line.

9. Apparatus for optical inspection of an object, comprising:
    an illumination assembly, which has a plane of symmetry that intersects the object along a line, and which comprises:
    first and second parallel rows of light sources, which are configured to emit light along respective optical axes, wherein the optical axes are oriented toward the object in respective first and second illumination planes that intersect the line at respective first and second equal and opposite elevation angles on opposing sides of the plane of symmetry; and
    first and second arrays of prisms, which are disposed respectively in the first and second illumination planes, and which are configured to divert the light emitted by the light sources so that the light incident on the object is concentrated within the first and second illumination planes, and is incident on the object from directions diagonal to the line within the first and second illumination planes; and
    an imaging assembly, which is configured to capture an image of a region of the object that contains the line under illumination by the illumination assembly.

10. The apparatus according to claim 9, wherein the prisms in the first and second arrays have prism axes that are respectively perpendicular to the first and second illumination planes, and are configured to refract the light so that the directions in which the light is diverted by the prisms fall within one of the first and second illumination planes.

11. The apparatus according to claim 10, wherein the light source and prisms are arranged so that at least a portion of the light impinging on the object intersects the line at intersection angles that are within 10° of the plane of symmetry.

12. Apparatus for optical inspection of an object, comprising:
    an illumination assembly, which has a plane of symmetry that intersects the object along a line, and which comprises multiple parallel rows of light sources for emitting light and illumination optics associated with each row for directing the light onto the object, the multiple parallel rows comprising:
    first and second rows of the light sources with respective first and second illumination optics that are configured to direct the light from the light sources in the first and second rows such that the light incident on the object is concentrated within respective first and second illumination planes that intersect the line at respective first and second equal and opposite elevation angles on opposing sides of the plane of symmetry; and
    third and fourth rows of the light sources with respective third and fourth illumination optics comprising arrays of prisms that are configured to divert the light from the light sources in the third and fourth rows such that the light incident on the object is concentrated within respective third and fourth illumination planes that intersect the line at respective third and fourth equal and opposite elevation angles on the opposing sides of the plane of symmetry; and
    an imaging assembly, which is configured to capture an image of the object under illumination by the multiple parallel rows of the light sources.

13. The apparatus according to claim 12, wherein the arrays of prisms are configured to divert the light emitted by the light sources so that the light impinges on the object along directions diagonal to the line.

14. The apparatus according to claim 13, wherein the arrays of the prisms have respective prism axes that are respectively perpendicular to the third and fourth illumination planes, and are configured to divert the light so that the directions in which the light is diverted by the prisms fall within one of the third and fourth illumination planes.

15. The apparatus according to claim 12, wherein the arrays of the prisms are configured to reflect the light from the light sources in the third and fourth rows toward the object.

16. Apparatus for optical inspection of an object, comprising:
   an illumination assembly, which has a plane of symmetry that intersects the object along a line, and which comprises:
      multiple parallel rows of light sources, which are configured to emit light in respective illumination planes that intersect the line on opposing sides of the plane of symmetry, wherein the multiple parallel rows of light sources comprise at least first and second rows of light sources; and
      illumination optics, which are configured to divert the light emitted by the first and second rows of light sources so that light incident on the object from the first and second rows of light sources is concentrated within first and second illumination planes that intersect the line at intersection angles that are within 10° of the plane of symmetry; and
   an imaging assembly, which is configured to capture an image of a region of the object that contains the line under illumination by the illumination assembly.

17. The apparatus according to claim 16, wherein the illumination optics are configured to divert the light emitted by the light sources so that at least some of the light impinges on the object along directions in the illumination planes that intersect the line at intersection angles that are within 5° of the plane of symmetry.

18. The apparatus according to claim 16, wherein the rows of the light sources have respective ends, and wherein the illumination assembly comprises at least one end mirror, adjacent and perpendicular to the ends of the rows, for reflecting at least a portion of the light diverted by the optics onto the object.

19. A method for optical inspection, comprising:
   illuminating an object under inspection using multiple parallel rows of light sources for emitting light and illumination optics associated with each row for directing the light onto the object, the multiple parallel rows comprising:
      at least a first row with first illumination optics comprising a first array of prisms that are configured to reflect the light emitted by the light sources in the first row; and
      at least a second row with second illumination optics comprising a second array of prisms that are configured to refract the light emitted by the light sources in the second row; and
   capturing an image of the object under illumination by the multiple parallel rows of the light sources.

20. The method according to claim 19, wherein the multiple parallel rows comprise at least a third row of the light sources with third illumination optics of a third type for illuminating the object directly, without incidence of light from the light sources in the third row on a prism array.

21. The method according to claim 19, wherein the light sources in at least some of the multiple parallel rows emit light of different, respective colors.

22. The method according to claim 19, wherein the light sources comprise light-emitting diodes (LEDs) having a rated maximum current, and wherein illuminating the object comprises driving the LEDs with current pulses in excess of the rated maximum current.

23. The method according to claim 19, wherein the illumination assembly has a plane of symmetry that intersects the object along a line, and wherein capturing the image comprises imaging a region of the object that contains at least a part of the line.

24. The method according to claim 23, and comprising scanning the illumination and imaging assemblies over the object in a direction perpendicular to the line.

25. The method according to claim 23, wherein the multiple parallel rows of the light sources are arranged in pairs of the rows, which define respective pairs of illumination planes that intersect the line at respective equal and opposite elevation angles on opposing sides of the plane of symmetry.

26. The method according to claim 23, wherein imaging the region comprises capturing respective images using a plurality of cameras, wherein the respective images are mutually adjacent and each contain a respective part of the line.

27. A method for optical inspection of an object, comprising:
   illuminating the object using an illumination assembly, which has a plane of symmetry that intersects the object along a line, and which comprises:
      first and second parallel rows of light sources, which are configured to emit light along respective optical axes, wherein the optical axes are oriented toward the object in respective first and second illumination planes that intersect the line at respective first and second equal and opposite elevation angles on opposing sides of the plane of symmetry; and
      first and second arrays of prisms, which are disposed respectively in the first and second illumination planes, and which are configured to divert the light emitted by the light sources so that the light incident on the object is concentrated within the first and second illumination planes, and is incident on the object from directions diagonal to the line within the first and second illumination planes; and
   capturing an image of a region of the object that contains the line under illumination by the illumination assembly.

28. The method according to claim 27, wherein the prisms in the first and second arrays have prism axes that are respectively perpendicular to the first and second illumination planes, and are configured to refract the light so that the directions in which the light is diverted by the prisms fall within one of the first and second illumination planes.

29. The method according to claim 28, wherein at least a portion of the light impinging on the object intersects the line at intersection angles that are within 10° of the plane of symmetry.

30. A method for optical inspection of an object, comprising:
   illuminating the object using an illumination assembly, which has a plane of symmetry that intersects the object along a line, and which comprises multiple parallel rows of light sources for emitting light and illumination optics associated with each row for directing the light onto the object, the multiple parallel rows comprising:
      first and second rows of the light sources with respective first and second illumination optics that are configured to direct the light from the light sources in the first and second rows such that the light incident on the object is concentrated within respective first and second illumination planes that intersect the line at respective first and second equal and opposite elevation angles on opposing sides of the plane of symmetry; and third and fourth rows of the light sources with respective third and fourth illumination optics comprising arrays of prisms that are configured to divert the light from the light sources in the third and fourth rows such that the light incident on the object is concentrated within respective third and fourth illumination planes that intersect the line at respective third and fourth equal and opposite elevation angles on the opposing sides of the plane of symmetry; and capturing an image of the object under illumination by the multiple parallel rows of the light sources.

31. The method according to claim 30, wherein the arrays of prisms are configured to divert the light emitted by the light sources so that the light impinges on the object along directions diagonal to the line.

32. The method according to claim 31, wherein the arrays of the prisms have respective prism axes that are respectively perpendicular to the third and fourth illumination planes, and are configured to divert the light so that the directions in which the light is diverted by the prisms fall within one of the third and fourth illumination planes.

33. The method according to claim 30, wherein the arrays of the prisms are configured to reflect the light from the light sources in the third and fourth rows toward the object.

34. A method for optical inspection of an object, comprising:

illuminating the object using an illumination assembly, which has a plane of symmetry that intersects the object along a line, and which comprises:

multiple parallel rows of light sources, which are configured to emit light in respective illumination planes that intersect the line on opposing sides of the plane of symmetry, wherein the multiple parallel rows of light sources comprise at least first and second rows of light sources; and illumination optics, which are configured to divert the light emitted by the first and second rows of light sources so that light incident on the object from the first and second rows of light sources is concentrated within first and second along illumination planes that intersect the line at intersection angles that are within 10° of the plane of symmetry; and an imaging assembly, which is configured to capture an image of a region of the object that contains the line under illumination by the illumination assembly.

35. The method according to claim 34, wherein the illumination optics are configured to divert the light emitted by the light sources so that at least some of the light impinges on the object along directions in the illumination planes that intersect the line at intersection angles that are within 5° of the plane of symmetry.

36. The method according to claim 34, wherein the rows of the light sources have respective ends, and wherein the illumination assembly comprises at least one end mirror, adjacent and perpendicular to the ends of the rows, for reflecting at least a portion of the light diverted by the optics onto the object.

* * * * *